US010352953B2

(12) United States Patent
Huber et al.

(10) Patent No.: US 10,352,953 B2
(45) Date of Patent: Jul. 16, 2019

(54) METHOD OF OPERATING A LABORATORY SAMPLE DISTRIBUTION SYSTEM, LABORATORY SAMPLE DISTRIBUTION SYSTEM AND A LABORATORY AUTOMATION SYSTEM

(71) Applicant: Roche Diagnostics Operations, Inc., Indianapolis, IN (US)

(72) Inventors: Tobias Huber, Backnang (DE); Achim Sinz, Waiblingen (DE); Namitha Mallikarjunaiah, Kornwestheim (DE); Oliver Denninger, Karlsruhe (DE); Mohammadreza Mahmudimanesh, Griesheim (DE); Timo Fleischmann, Esslingen (DE); Domenic Jenz, Esslingen (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 15/154,144

(22) Filed: May 13, 2016

(65) Prior Publication Data

US 2016/0341751 A1    Nov. 24, 2016

(30) Foreign Application Priority Data

May 22, 2015   (EP) .................... 15168780

(51) Int. Cl.
*G01N 35/04* (2006.01)
*G01N 35/00* (2006.01)
*B65G 43/00* (2006.01)

(52) U.S. Cl.
CPC ......... *G01N 35/0092* (2013.01); *B65G 43/00* (2013.01); *G01N 35/00584* (2013.01);
(Continued)

(58) Field of Classification Search
CPC ..... G01N 35/00712; G01N 2035/0094; G01N 2035/0462; B01N 2035/0477; B65G 54/02
See application file for complete search history.

(56) References Cited

U.S. PATENT DOCUMENTS 3,273,727 A   9/1966   Rogers et al.
3,653,485 A   4/1972   Donlon
(Continued)

FOREIGN PATENT DOCUMENTS

CN   201045617 Y   4/2008
CN   102109530 A   6/2011
(Continued)

OTHER PUBLICATIONS

Hart, Peter E., Nils J. Nilsson and Bertram Raphael, "A Formal Basis for the Heuristic Determination of Minimum Cost Paths," IEEE Transactions of Systems Science and Cybernetics, vol. SSC-4, No. 2. Jul. 1968: pp. 100-107.*
(Continued)

*Primary Examiner* — Kathryn Wright
(74) *Attorney, Agent, or Firm* — Roche Diagnostics Operations, Inc.

(57) ABSTRACT

A method of operating a laboratory sample distribution system is disclosed. The laboratory sample distribution system comprises a plurality of sample container carriers. The sample container carriers carry one or more sample containers. The sample containers comprise samples to be analyzed by a plurality of laboratory stations. The system also comprises a transport plane. The transport plane supports the sample container carriers. The transport plane comprises a plurality of transfer locations. The transfer locations are assigned to corresponding laboratory stations. The system also comprises a drive. The drive moves the sample container carriers on the transport plane. The method
(Continued)

comprises, during an initialization of the laboratory sample distribution system, pre-calculating routes depending on the transfer locations and, after the initialization of the laboratory sample distribution system, controlling the drive such that the sample container carriers move along the pre-calculated routes.

14 Claims, 2 Drawing Sheets

(52) U.S. Cl.
CPC ..... *G01N 35/04* (2013.01); *G01N 2035/0406* (2013.01); *G01N 2035/0462* (2013.01); *G01N 2035/0477* (2013.01)

(56) References Cited

U.S. PATENT DOCUMENTS

| | | | |
|---|---|---|---|
| 3,901,656 A | 8/1975 | Durkos et al. |
| 4,150,666 A | 4/1979 | Brush |
| 4,395,164 A | 7/1983 | Beltrop |
| 4,544,068 A | 10/1985 | Cohen |
| 4,771,237 A | 9/1988 | Daley |
| 5,120,506 A | 6/1992 | Saito et al. |
| 5,295,570 A | 3/1994 | Grechsch et al. |
| 5,309,049 A | 5/1994 | Kawada et al. |
| 5,457,368 A | 10/1995 | Jacobsen et al. |
| 5,523,131 A | 6/1996 | Isaacs et al. |
| 5,530,345 A | 6/1996 | Murari et al. |
| 5,636,548 A | 6/1997 | Dunn et al. |
| 5,641,054 A | 6/1997 | Mori et al. |
| 5,651,941 A | 7/1997 | Stark et al. |
| 5,720,377 A | 2/1998 | Lapeus et al. |
| 5,735,387 A | 4/1998 | Polaniec et al. |
| 5,788,929 A | 8/1998 | Nesti |
| 6,045,319 A | 4/2000 | Uchida et al. |
| 6,062,398 A | 5/2000 | Talmayr |
| 6,141,602 A | 10/2000 | Igarashi et al. |
| 6,151,535 A | 11/2000 | Ehlers |
| 6,184,596 B1 | 2/2001 | Ohzeki |
| 6,191,507 B1 | 2/2001 | Peltier et al. |
| 6,206,176 B1 | 3/2001 | Blonigan et al. |
| 6,255,614 B1 | 7/2001 | Yamakawa et al. |
| 6,260,360 B1 | 7/2001 | Wheeler |
| 6,279,728 B1 | 8/2001 | Jung et al. |
| 6,293,750 B1 | 9/2001 | Cohen et al. |
| 6,429,016 B1 | 8/2002 | McNeil |
| 6,444,171 B1 | 9/2002 | Sakazume et al. |
| 6,571,934 B1 | 6/2003 | Thompson et al. |
| 7,028,831 B2 | 4/2006 | Veiner |
| 7,078,082 B2 | 7/2006 | Adams |
| 7,122,158 B2 | 10/2006 | Itoh |
| 7,278,532 B2 | 10/2007 | Martin |
| 7,326,565 B2 | 2/2008 | Yokoi et al. |
| 7,425,305 B2 | 9/2008 | Itoh |
| 7,428,957 B2 | 9/2008 | Schaefer |
| 7,578,383 B2 | 8/2009 | Itoh |
| 7,597,187 B2 | 10/2009 | Bausenwein et al. |
| 7,850,914 B2 | 12/2010 | Veiner et al. |
| 7,858,033 B2 | 12/2010 | Itoh |
| 7,875,254 B2 | 1/2011 | Garton |
| 7,939,484 B1 | 5/2011 | Loeffler et al. |
| 8,240,460 B1 | 8/2012 | Bleau et al. |
| 8,281,888 B2 | 10/2012 | Bergmann |
| 8,502,422 B2 | 8/2013 | Lykkegaard |
| 8,796,186 B2 | 8/2014 | Shirazi |
| 8,833,544 B2 | 9/2014 | Stoeckle et al. |
| 9,211,543 B2 | 12/2015 | Ohga et al. |
| 9,239,335 B2 | 1/2016 | Heise |
| 2002/0009391 A1 | 1/2002 | Marquiss et al. |
| 2003/0092185 A1 | 5/2003 | Qureshi et al. |
| 2004/0050836 A1 | 3/2004 | Nesbitt et al. |
| 2004/0084531 A1 | 5/2004 | Itoh |
| 2005/0061622 A1 | 3/2005 | Martin |
| 2005/0109580 A1 | 5/2005 | Thompson |
| 2005/0194333 A1 | 9/2005 | Veiner et al. |
| 2005/0196320 A1 | 9/2005 | Veiner et al. |
| 2005/0226770 A1 | 10/2005 | Allen et al. |
| 2005/0242963 A1 | 11/2005 | Oldham et al. |
| 2005/0247790 A1 | 11/2005 | Itoh |
| 2005/0260101 A1 | 11/2005 | Nauck et al. |
| 2005/0271555 A1 | 12/2005 | Itoh |
| 2006/0000296 A1 | 1/2006 | Salter |
| 2006/0047303 A1 | 3/2006 | Ortiz et al. |
| 2006/0219524 A1 | 10/2006 | Kelly et al. |
| 2007/0116611 A1 | 5/2007 | DeMarco |
| 2007/0210090 A1 | 9/2007 | Sixt et al. |
| 2007/0248496 A1 | 10/2007 | Bondioli et al. |
| 2007/0276558 A1 | 11/2007 | Kim |
| 2008/0012511 A1 | 1/2008 | Ono |
| 2008/0029368 A1 | 2/2008 | Komori |
| 2008/0056328 A1 | 3/2008 | Rund et al. |
| 2008/0131961 A1 | 6/2008 | Crees et al. |
| 2008/0286162 A1 | 11/2008 | Onizawa et al. |
| 2009/0004732 A1 | 1/2009 | LaBarre et al. |
| 2009/0022625 A1 | 1/2009 | Lee et al. |
| 2009/0081771 A1 | 3/2009 | Breidford et al. |
| 2009/0128139 A1 | 5/2009 | Drenth |
| 2009/0142844 A1 | 6/2009 | LeComte |
| 2009/0180931 A1 | 7/2009 | Silbert et al. |
| 2009/0322486 A1 | 12/2009 | Gerstel |
| 2010/0000250 A1 | 1/2010 | Sixt |
| 2010/0152895 A1 | 6/2010 | Dai |
| 2010/0175943 A1 | 7/2010 | Bergmann |
| 2010/0186618 A1 | 7/2010 | King et al. |
| 2010/0255529 A1 | 10/2010 | Cocola et al. |
| 2010/0300831 A1 | 12/2010 | Pedrazzini |
| 2010/0312379 A1 | 12/2010 | Pedrazzini |
| 2011/0050213 A1 | 3/2011 | Furukawa |
| 2011/0124038 A1 | 5/2011 | Bishop et al. |
| 2011/0172128 A1 | 7/2011 | Davies et al. |
| 2011/0186406 A1 | 8/2011 | Kraus |
| 2011/0287447 A1 | 11/2011 | Norderhaug |
| 2012/0037696 A1 | 2/2012 | Lavi |
| 2012/0129673 A1 | 5/2012 | Fukugaki et al. |
| 2012/0178170 A1 | 7/2012 | Van Praet |
| 2012/0211645 A1 | 8/2012 | Tullo et al. |
| 2012/0275885 A1 | 11/2012 | Furrer et al. |
| 2012/0282683 A1 | 11/2012 | Mototsu |
| 2012/0295358 A1 | 11/2012 | Ariff et al. |
| 2012/0310401 A1 | 12/2012 | Shah |
| 2013/0034410 A1 | 2/2013 | Heise et al. |
| 2013/0126302 A1 | 5/2013 | Johns et al. |
| 2013/0153677 A1 | 6/2013 | Leen et al. |
| 2013/0180824 A1 | 7/2013 | Kleinikkink et al. |
| 2013/0263622 A1 | 10/2013 | Mullen et al. |
| 2013/0322992 A1 | 12/2013 | Pedrazzini |
| 2014/0170023 A1 | 6/2014 | Saito et al. |
| 2014/0202829 A1* | 7/2014 | Eberhardt ............ G01N 35/04 198/341.01 |
| 2014/0231217 A1 | 8/2014 | Denninger et al. |
| 2014/0234065 A1 | 8/2014 | Heise et al. |
| 2014/0234949 A1 | 8/2014 | Wasson et al. |
| 2015/0014125 A1 | 1/2015 | Hecht |
| 2015/0166265 A1 | 6/2015 | Pollack et al. |
| 2015/0233956 A1 | 8/2015 | Buehr |
| 2015/0233957 A1 | 8/2015 | Riether |
| 2015/0241457 A1 | 8/2015 | Miller |
| 2015/0273468 A1 | 10/2015 | Croquette et al. |
| 2015/0273691 A1 | 10/2015 | Pollack |
| 2015/0276775 A1 | 10/2015 | Mellars et al. |
| 2015/0276776 A1 | 10/2015 | Riether |
| 2015/0276777 A1 | 10/2015 | Riether |
| 2015/0276778 A1 | 10/2015 | Riether |
| 2015/0276781 A1 | 10/2015 | Riether |
| 2015/0276782 A1 | 10/2015 | Riether |
| 2015/0360876 A1 | 12/2015 | Sinz |
| 2015/0360878 A1 | 12/2015 | Denninger et al. |
| 2016/0003859 A1 | 1/2016 | Wenczel et al. |
| 2016/0025756 A1 | 1/2016 | Pollack et al. |
| 2016/0054341 A1 | 2/2016 | Edelmann |
| 2016/0054344 A1 | 2/2016 | Heise et al. |

(56) References Cited

U.S. PATENT DOCUMENTS

| | | |
|---|---|---|
| 2016/0069715 A1 | 3/2016 | Sinz |
| 2016/0077120 A1 | 3/2016 | Riether |
| 2016/0097786 A1 | 4/2016 | Malinkowski et al. |
| 2016/0229565 A1 | 8/2016 | Margner |
| 2016/0274137 A1 | 9/2016 | Baer |
| 2016/0282378 A1 | 9/2016 | Malinowski et al. |
| 2016/0341750 A1 | 11/2016 | Sinz et al. |
| 2017/0059599 A1 | 3/2017 | Riether |
| 2017/0096307 A1 | 4/2017 | Mahmudimanesh et al. |
| 2017/0097372 A1 | 4/2017 | Heise et al. |
| 2017/0101277 A1 | 4/2017 | Malinowski |
| 2017/0108522 A1 | 4/2017 | Baer |
| 2017/0131307 A1 | 5/2017 | Pedain |
| 2017/0131309 A1 | 5/2017 | Pedain |
| 2017/0131310 A1 | 5/2017 | Volz et al. |
| 2017/0138971 A1 | 5/2017 | Heise et al. |
| 2017/0160299 A1 | 6/2017 | Schneider et al. |
| 2017/0168079 A1 | 6/2017 | Sinz |
| 2017/0174448 A1 | 6/2017 | Sinz |
| 2017/0184622 A1 | 6/2017 | Sinz et al. |
| 2017/0248623 A1 | 8/2017 | Kaeppeli et al. |
| 2017/0248624 A1 | 8/2017 | Kaeppeli et al. |
| 2017/0363608 A1 | 12/2017 | Sinz |
| 2018/0067141 A1 | 3/2018 | Mahmudimanesh et al. |
| 2018/0074087 A1 | 3/2018 | Heise et al. |
| 2018/0106821 A1 | 4/2018 | Vollenweider et al. |
| 2018/0128848 A1 | 5/2018 | Schneider et al. |
| 2018/0156835 A1 | 6/2018 | Hassan |
| 2018/0188280 A1 | 7/2018 | Malinowski |
| 2018/0210000 A1 | 7/2018 | van Mierlo |
| 2018/0210001 A1 | 7/2018 | Reza |
| 2018/0217174 A1 | 8/2018 | Malinowski |
| 2018/0217176 A1 | 8/2018 | Sinz et al. |
| 2018/0224476 A1 | 8/2018 | Birrer et al. |
| 2018/0348244 A1 | 12/2018 | Ren |
| 2018/0348245 A1 | 12/2018 | Schneider et al. |
| 2019/0018027 A1 | 1/2019 | Hoehnel |
| 2019/0076845 A1 | 3/2019 | Huber et al. |
| 2019/0076846 A1 | 3/2019 | Durco et al. |
| 2019/0086433 A1 | 3/2019 | Hermann et al. |
| 2019/0094251 A1 | 3/2019 | Malinowski |
| 2019/0094252 A1 | 3/2019 | Waser et al. |
| 2019/0101468 A1 | 4/2019 | Haldar |

FOREIGN PATENT DOCUMENTS

| | | |
|---|---|---|
| DE | 3909786 A1 | 9/1990 |
| DE | 102012000665 A1 | 8/2012 |
| DE | 102011090044 A1 | 7/2013 |
| EP | 0601213 A1 | 10/1992 |
| EP | 0775650 A1 | 5/1997 |
| EP | 0896936 A1 | 2/1999 |
| EP | 0916406 A2 | 5/1999 |
| EP | 1122194 A1 | 8/2001 |
| EP | 1524525 A1 | 4/2005 |
| EP | 2119643 A1 | 11/2009 |
| EP | 2148117 A1 | 1/2010 |
| EP | 2327646 A1 | 6/2011 |
| EP | 2447701 A2 | 5/2012 |
| EP | 2500871 A1 | 9/2012 |
| EP | 2502675 A1 | 9/2012 |
| EP | 2887071 A1 | 6/2015 |
| GB | 2165515 A | 4/1986 |
| JP | S56-147209 A | 11/1981 |
| JP | 60-223481 A | 11/1985 |
| JP | 61-081323 A | 4/1986 |
| JP | S61-069604 A | 4/1986 |
| JP | S61-094925 A | 5/1986 |
| JP | S61-174031 A | 8/1986 |
| JP | S61-217434 A | 9/1986 |
| JP | S62-100161 A | 5/1987 |
| JP | S63-31918 A | 2/1988 |
| JP | S63-48169 A | 2/1988 |
| JP | S63-82433 U | 5/1988 |
| JP | S63-290101 A | 11/1988 |
| JP | 01-148966 A | 6/1989 |
| JP | H01-266860 A | 10/1989 |
| JP | H02-87903 A | 3/1990 |
| JP | 03-192013 A | 8/1991 |
| JP | H03-38704 Y2 | 8/1991 |
| JP | H04-127063 A | 4/1992 |
| JP | H05-69350 A | 3/1993 |
| JP | H05-142232 A | 6/1993 |
| JP | H05-180847 A | 7/1993 |
| JP | 06-268808 A | 4/1994 |
| JP | H06-148198 A | 5/1994 |
| JP | 06-156730 A | 6/1994 |
| JP | 06-211306 A | 8/1994 |
| JP | 07-228345 A | 8/1995 |
| JP | 07-236838 A | 9/1995 |
| JP | H07-301637 A | 11/1995 |
| JP | H09-17848 A | 1/1997 |
| JP | H11-083865 A | 3/1999 |
| JP | H11-264828 A | 9/1999 |
| JP | H11-304812 A | 11/1999 |
| JP | H11-326336 A | 11/1999 |
| JP | 2000-105243 A | 4/2000 |
| JP | 2000-105246 A | 4/2000 |
| JP | 3112393 B2 | 9/2000 |
| JP | 2001-124786 A | 5/2001 |
| JP | 2001-240245 A | 9/2001 |
| JP | 2005-001055 A | 1/2005 |
| JP | 2005-249740 A | 9/2005 |
| JP | 2006-106008 A | 4/2006 |
| JP | 2007-309675 A | 11/2007 |
| JP | 2007-314262 A | 12/2007 |
| JP | 2007-315835 A | 12/2007 |
| JP | 2007-322289 A | 12/2007 |
| JP | 2009-036643 A | 2/2009 |
| JP | 2009-062188 A | 3/2009 |
| JP | 2009-145188 A | 7/2009 |
| JP | 2009-300402 A | 12/2009 |
| JP | 2010-243310 A | 10/2010 |
| JP | 2013-172009 A | 9/2013 |
| JP | 2013-190400 A | 9/2013 |
| SU | 685591 A1 | 9/1979 |
| WO | 1996/036437 A1 | 11/1996 |
| WO | 2003/042048 A3 | 5/2003 |
| WO | 2007/024540 A1 | 3/2007 |
| WO | 2008/133708 A1 | 11/2008 |
| WO | 2009/002358 A1 | 12/2008 |
| WO | 2010/042722 A1 | 4/2010 |
| WO | 2012/170636 A1 | 7/2010 |
| WO | 2010/087303 A1 | 8/2010 |
| WO | 2010/129715 A1 | 11/2010 |
| WO | 2011/138448 A1 | 11/2011 |
| WO | 2012/158520 A1 | 11/2012 |
| WO | 2012/158541 A1 | 11/2012 |
| WO | 2013/064656 A1 | 5/2013 |
| WO | 2013/099647 A1 | 7/2013 |
| WO | 2013/152089 A1 | 10/2013 |
| WO | 2013/169778 A1 | 11/2013 |
| WO | 2013/177163 A1 | 11/2013 |
| WO | 2014/050821 A1 | 4/2014 |
| WO | 2014/059134 A1 | 4/2014 |
| WO | 2014/071214 A1 | 5/2014 |

OTHER PUBLICATIONS

Russell Stuart and Peter Norvig, Artificial Intelligence: A Modern Approach. Pearson Education, 2011, 3rd Edition.*

Stentz, Anthony, "Optimal and Efficient Path Planning for Partially-Known Environments," IEEE International Conference on Robotics and Automation, May 1994.*

* cited by examiner

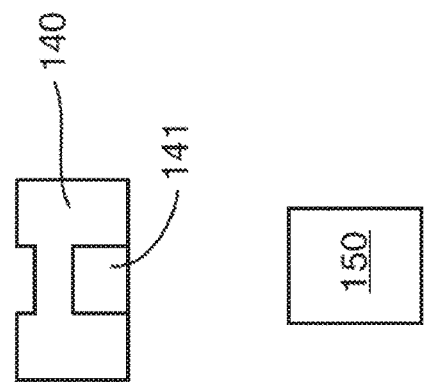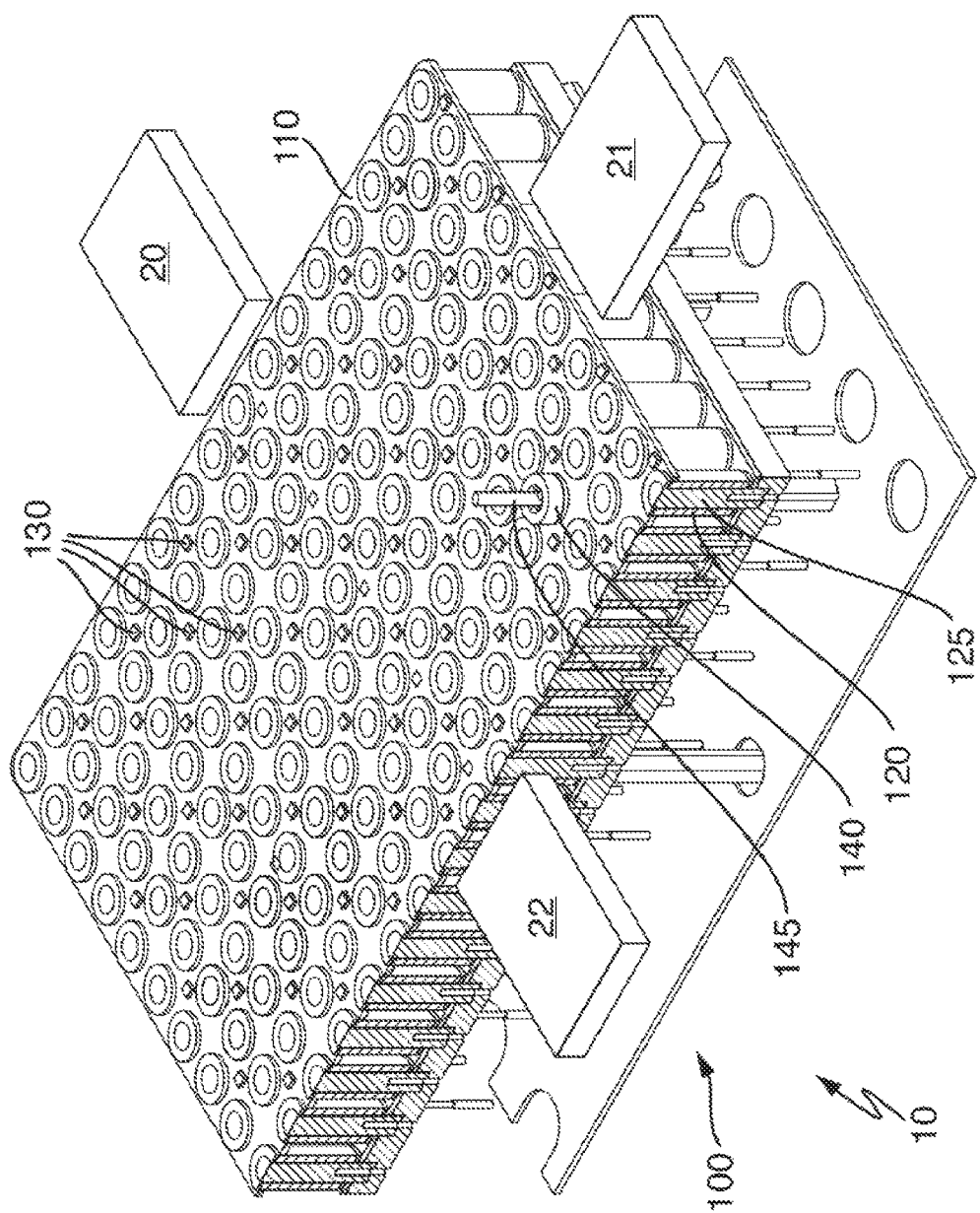
Fig. 1

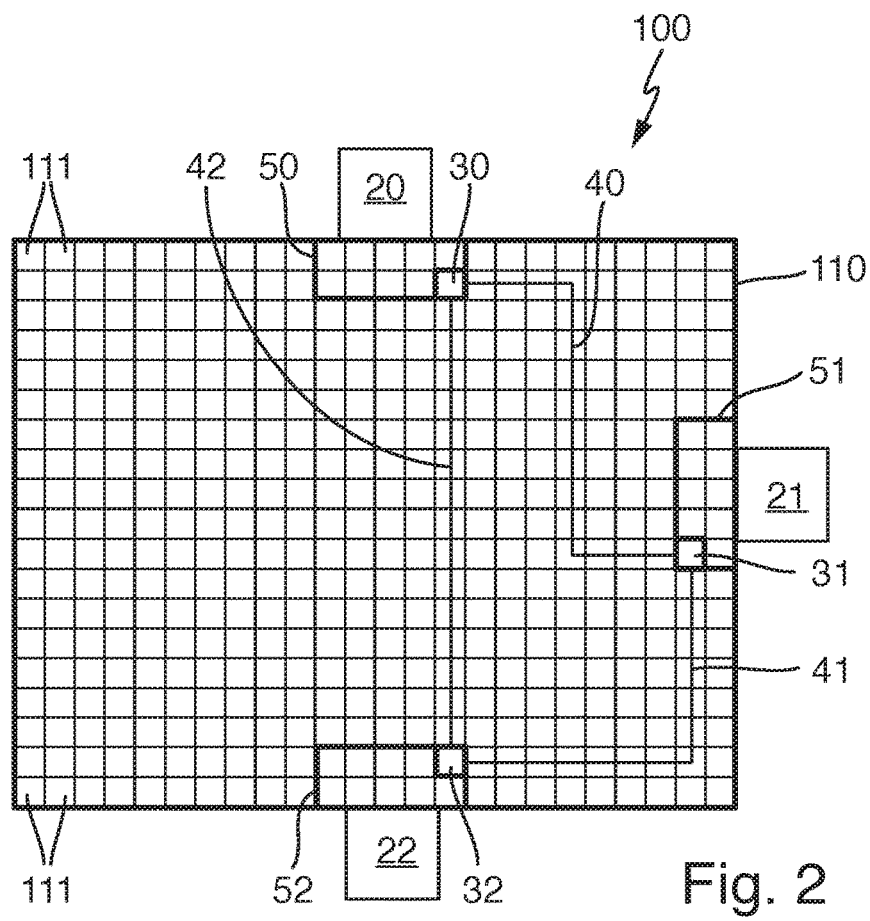
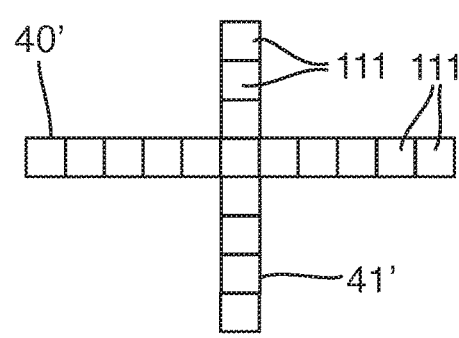
Fig. 3

METHOD OF OPERATING A LABORATORY SAMPLE DISTRIBUTION SYSTEM, LABORATORY SAMPLE DISTRIBUTION SYSTEM AND A LABORATORY AUTOMATION SYSTEM

CROSS-REFERENCE TO RELATED APPLICATIONS

This application claims priority to EP 15168780.3, filed May 22, 2015, which is hereby incorporated by reference.

BACKGROUND

The present disclosure relates to a method of operating a laboratory sample distribution system, a laboratory sample distribution system, and a laboratory automation system.

Laboratory sample distribution systems can be used in order to distribute samples between pluralities of laboratory stations in a laboratory automation system. For example, a two-dimensional laboratory sample distribution system providing high throughput is known. Electro-magnetic actuators are disposed below a transport plane in order to drive sample container carriers carrying sample containers on the transport plane.

There is a need for a method of operating a laboratory sample distribution system, a laboratory sample distribution system and a laboratory automation system enabling an efficient and reliable distribution of samples between different laboratory stations.

SUMMARY

According to the present disclosure, a method and a laboratory sample distribution system are presented. The laboratory sample distribution system can comprise a plurality of sample container carriers. The sample container carriers can be adapted to carry one or more sample containers. The sample containers can comprise samples to be analyzed by a plurality of laboratory stations. The system can further comprise a transport plane. The transport plane can be adapted to support the sample container carriers. The transport plane can comprise a plurality of transfer locations. The transfer locations can be assigned to corresponding laboratory stations. The system can also comprise a drive. The drive can be adapted to move the sample container carriers on the transport plane. The system can also comprise a control unit. The control unit can be adapted to pre-calculate routes depending on the transfer locations during an initialization of the laboratory sample distribution system and to control the drive such that the sample container carriers can move along the pre-calculated routes after the initialization of the laboratory sample distribution system.

Accordingly, it is a feature of the embodiments of the present disclosure to provide for a method of operating a laboratory sample distribution system, a laboratory sample distribution system and a laboratory automation system enabling an efficient and reliable distribution of samples between different laboratory stations. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which:

FIG. 1 illustrates schematically a laboratory automation system in a perspective view according to an embodiment of the present disclosure.

FIG. 2 illustrates schematically the laboratory automation system of FIG. 1 in a top view according to an embodiment of the present disclosure.

FIG. 3 illustrates shows different pre-calculated routes comprising reserved fields according to an embodiment of the present disclosure.

DETAILED DESCRIPTION

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

The method can be adapted to operate a laboratory sample distribution system. The laboratory sample distribution system can comprises a number (e.g., 10 to 10000) of sample container carriers. The sample container carriers can be respectively adapted to carry one or more sample containers. The sample containers can respectively comprise samples to be analyzed by a plurality (e.g., 2 to 50) of laboratory stations.

The laboratory sample distribution system can further comprise a, substantially planar, transport plane. The transport plane can be adapted to support the sample container carriers, i.e. the sample container carriers can be placed on top of the transport plane and can be moved on top of and over the transport plane.

The transport plane can comprise a plurality (e.g., 2 to 100) of transfer locations, or nodes. The transfer locations, or nodes, can be assigned to corresponding laboratory stations. For example, each laboratory station may have a single corresponding transfer location, or node. Alternatively, more than one transfer location, or node, may be assigned to a corresponding laboratory station. The transfer locations, or nodes, may be statically, or dynamically, assigned to the laboratory stations. In other words, during operation, the transfer locations may be changed, if necessary.

The laboratory sample distribution system can further comprise a drive. The drive can be adapted to move the sample container carriers on and over the transport plane.

The operating method can comprise, during an initialization (i.e., starting and/or booting) of the laboratory sample distribution system e.g., fixed routes extending over the transport plane can be pre-calculated depending on, e.g., between, the different transfer locations. In other words, the pre-calculated routes can be provided on the transport plane between the transfer locations. The transfer locations may represent initial, or goal, nodes in the sense of Graph theory.

After the initialization of the laboratory sample distribution system during a normal operational mode, the drive can be controlled such that the sample container carriers can move along the pre-calculated routes over the transport plane, if and when the sample container carriers are to be distributed between the different laboratory stations. In other words, after the initialization of the laboratory sample distribution system during a normal operational mode, the drive can be controlled such that the sample container carriers can repeatedly move, for example, only, along the pre-calculated fixed routes over the transport plane, if and when the sample container carriers are to be distributed between the different laboratory stations. The term "fixed" can denote that the routes can be statically calculated (i.e. not recalculated) and that the calculated routes can be used by several sample container carriers and may not be calculated for each sample container carrier individually. Self-evidently, in specific use scenarios, the sample container carriers may move apart from the pre-calculated routes, e.g., in case the sample container carriers have to be removed from the transport plane and/or in error conditions. Further, empty sample container carriers may move along different routes and/or apart from the pre-calculated routes.

The routes can be calculated using an informed search algorithm such as, for example, an A*-algorithm or a D*-algorithm. The A*-algorithm is an algorithm that can be used in path finding and graph traversal to efficiently calculate a traversable path between different nodes, e.g., in the form of the transfer locations. The A*-algorithm uses a best-first search and can find a least-cost path from a given initial node to one goal node (out of one or more possible goals). As the A*-algorithm traverses the graph, it can follow a path of the lowest expected total cost or distance, keeping a sorted priority queue of alternate path segments along the way. The D*-algorithm is a refined A*-algorithm.

The routes can be calculated such that a number of intersections between different routes can be minimized.

During the initialization of the laboratory sample distribution system, respective buffer areas located on the transport plane can be logically allocated to the laboratory stations. Samples waiting to be analyzed by the laboratory stations can be buffered in the buffer areas. For example, each laboratory station may have a single corresponding buffer area on the transport plane. Alternatively, more than one buffer area may be assigned to a corresponding laboratory station on the transport plane. The buffer areas can be allocated such that the pre-calculated routes do not intersect the buffer areas.

The sample container carriers can be entered into the buffer areas or can be removed from the buffer areas exclusively over (passing) the transfer locations, i.e., the transfer locations can serve as a gate (entrance/exit) to the buffer areas.

The transport plane can be segmented into logical fields, e.g., square shaped logical fields of substantially identical size and outline. The logical fields can be arranged in a chess board manner. In a time-prioritized reservation scheme, an adjustable number (e.g., 1 to 100) of logical fields positioned on or lying on a pre-calculated route can respectively be reserved for sample container carriers to be moved. In other words, the logical fields can be reserved in a first come, first serve manner for each sample container carrier to be moved. The logical fields can typically be reserved before starting a movement of a sample container carrier. Nevertheless, the logical fields can be reserved during a movement of a sample container carrier, if the sample container carrier has not yet reached the logical fields to be reserved. A sample container carrier moving on a route comprising logical fields being reserved for another sample container carrier with a higher time priority, i.e., the logical fields have been reserved for the other sample container carrier prior to the reservation for the moving sample container, can be stopped before the reserved field or may not be started. The reserved fields can be released when the sample container carrier has passed the reserved field(s).

After the initialization of the laboratory sample distribution system, operating data of the laboratory sample distribution system can be collected and stored. During a next initialization of the laboratory sample distribution system, the routes can be pre-calculated depending on the transfer locations and depending on the operating data.

The operating data can comprise information regarding a volume of traffic on the routes. The information regarding the volume of traffic can comprise information of the number of sample container carriers being moved on the route per time unit (e.g., per minute/hour/day etc.). A time profile of the volume of traffic over the operating time may be determined.

The step of pre-calculating the routes can comprise that a number of lanes assigned to the routes can be determined depending on the volume of traffic. For example, in case of low volume of traffic, a single lane may be assigned to a route. In case of increasing volume of traffic, two or more lanes may be assigned to the route. The routes can be, in one embodiment, one-way lanes.

Samples, and/or sample containers, and/or the sample container carriers can be transferred to/from the laboratory stations using the transfer locations. For example, a pick-and-place device can pick a sample container comprised in a sample container carrier located at one of the transfer locations and can transfer the sample container to the laboratory station. Accordingly, a sample container can be transferred from one of the laboratory stations to an empty sample container carrier located on the transfer location.

During the initialization of the laboratory sample distribution system, the routes can be pre-calculated between the transfer locations, i.e., the end points, or end nodes, of the routes can be formed by the transfer locations. If, for example, a first, a second, and a third transfer location are given, a route between the first and the second transfer location, a route between the first and the third transfer location, and a route between the second and the third transfer location can be pre-calculated.

The laboratory sample distribution system can be adapted to perform the method as described above.

The laboratory sample distribution system can comprise a plurality of sample container carriers. The sample container carriers can be adapted to carry one or more sample containers. The sample containers can comprise samples to be analyzed by a plurality of laboratory stations. The system can also comprise a transport plane. The transport plane can be adapted to support the sample container carriers. The transport plane can comprise a plurality of transfer locations The transfer locations can be assigned to corresponding laboratory stations. The system can also comprise a drive. The drive can be adapted to move the sample container carriers on the transport plane. The system can also comprise a control unit such as, for example, in the form of a microprocessor and program storage. The control unit can be adapted to control the laboratory sample distribution system such that the method as described above can be performed. The control unit can be adapted to pre-calculate routes depending on the transfer locations during an initialization of the laboratory sample distribution system and to control the drive such that the sample container carriers can move along the pre-calculated routes after the initialization of the laboratory sample distribution system.

The sample container carriers can comprise at least one magnetically active device such as, for example, at least one permanent magnet. The drive can comprise a plurality of electro-magnetic actuators being stationary arranged in rows and columns below the transport plane. The electro-magnetic actuators can be adapted to apply a magnetic force to the sample container carriers. The control unit can be adapted to activate the electromagnetic actuators such that the sample container carriers can move simultaneously and independently from one another along the pre-calculated routes. The electro-magnetic actuators may define corresponding nodes of a graph in the sense of Graph Theory. A node may be defined or located on the transport plane above the corresponding electro-magnetic actuator. The transfer locations may be formed above a corresponding electro-magnetic actuator. The so defined grid-shaped graph may be used by an informed search algorithm such as, for example, an A*-algorithm or a D*-algorithm, to calculate a traversable path from initial node, or an initial transfer, location to a goal node, or a goal transfer location.

The laboratory automation system comprises a plurality (e.g., 2 to 50) of laboratory stations such as, for example, pre-analytical, analytical and/or post-analytical stations, and a laboratory sample distribution system as described above.

Pre-analytical stations may be adapted to perform any kind of pre-processing of samples, sample containers and/or sample container carriers. Analytical stations may be adapted to use a sample or part of the sample and a reagent to generate a measuring signal, the measuring signal indicating if and in which concentration, if any, an analyte exists. Post-analytical stations may be adapted to perform any kind of post-processing of samples, sample containers and/or sample container carriers.

The pre-analytical, analytical and/or post-analytical stations may comprise at least one of a decapping station, a recapping station, a centrifugation station, an archiving station, a pipetting station, a sorting station, a tube type identification station, and a sample quality determining station.

The pre-calculated routes can be visualized on the transport plane, such that an operator can control the pre-calculated routes and, if necessary, manually adjust the pre-calculated routes. In order to visualize the pre-calculated routes visualizing means e.g., in the form of light emitting devices such as LEDs can be arranged below the transport plane. The transport plane can be at least partially translucent. For example, for each electro-magnetic actuator, a corresponding LED may be provided placed adjacent to the electro-magnetic actuator. The visualizing means may further be used to visualize the operating state of the corresponding electro-magnetic actuator and may, for example, indicate if the corresponding electro-magnetic actuator is defective. Additionally, if the transport plane is segmented into a number of separate modules, defective modules may be signalized by the visualizing means located inside the defective module.

Referring initially to FIG. 1, FIG. 1 schematically shows a laboratory automation system 10 in a perspective view. The laboratory automation system 10 can comprise three laboratory stations 20, 21, 22, e.g., pre-analytical, analytical and/or post-analytical stations, and a laboratory sample distribution system 100. Self-evidently, the laboratory automation system 10 may comprise more than three laboratory stations 20, 21, 22.

The laboratory sample distribution system 100 can comprises a plurality of sample container carriers 140. For the sake of explanation, only a single sample container carrier 140 is depicted. Self-evidently, the laboratory sample distribution system 100 can comprise a plurality of sample container carriers 140, e.g., 50 to 500 sample container carriers 140. The sample container carriers 140 can respectively comprise a magnetically active device 141 in the form of a permanent magnet.

The sample container carriers 140 can be adapted to carry one or more sample containers 145. The sample containers 145 can comprise samples to be analyzed by the laboratory stations 20, 21, 22.

The laboratory sample distribution system 100 can further comprises a transport plane 110. The transport plane 110 can be adapted to support or carry the sample container carriers 140.

Positions sensors 130, e.g., in form of Hall sensors, can be distributed over the transport plane 110, such that a location of a respective sample container carrier 140 can be detected.

Referring to FIG. 2, the transport plane 110 can comprise a plurality of logical transfer locations 30, 31, 32. The transfer location 30 can be logically allocated to the laboratory station 20, the transfer location 31 can be logically allocated to the laboratory station 21 and the transfer location 32 can be logically allocated to the laboratory station 22. The transport plane 110 can comprises a plurality of logical buffer areas 50, 51, 52. The buffer area 50 can be logically allocated to the laboratory station 20, the buffer area 51 can be logically allocated to the laboratory station 21, and the buffer area 52 can be logically allocated to the laboratory station 22. Samples waiting to be analyzed by the laboratory stations 20, 21, 22 can be buffered in the respective buffer areas 50, 51, 52. Sample container carriers 140 can enter the buffer areas 50, 51, 52 or can be removed from the buffer areas 50, 51, 52 exclusively over the corresponding transfer locations 30, 31, 32.

Referring to FIG. 1 again, the laboratory sample distribution system 100 can further comprises a drive. The drive can comprise a plurality of electro-magnetic actuators 120 being stationary arranged in rows and columns below the transport plane 110. The electro-magnetic actuators 120 can respectively comprise a coil surrounding a ferromagnetic core 125. The electro-magnetic actuators 120 can be adapted to apply a magnetic drive force to the container carriers 140.

The laboratory sample distribution system 100 can further comprise a control unit 150. The control unit 150 can, inter alia, control the electro-magnetic actuators 120 such that the sample container carriers 140 may move simultaneously and independently from one another over the transport plane 110.

The method of operation of the laboratory sample distribution system 100 will be described with respect to FIGS. 2 and 3.

FIG. 2 schematically shows the laboratory automation system 10 of FIG. 1 in a top view. During an initialization, or start-up phase, of the laboratory sample distribution system 100, the control unit 150 can pre-calculate routes 40, 41, 42 between the transfer locations 30, 31, 32. In addition, during the initialization of the laboratory sample distribution system 100, the buffer areas 50, 51, 52 can be logically allocated to the laboratory station 20, 21, 22, respectively.

After the initialization of the laboratory sample distribution system 100, the control unit 150 can control the electro-magnetic actuators 120 such that the sample container carriers 140 can move along the pre-calculated routes 40, 41, 42, if the sample container carriers 140 have to be distributed between the laboratory stations 20, 21, 22.

The routes 40, 41, 42 can be calculated using an A*-algorithm. The routes 40, 41, 42 can be, inter alia, calculated such that a number of intersections between different routes 40, 41, 42 can be minimized. In the embodiment depicted, no intersections occur.

Referring to FIGS. 2 and 3, the transport plane 110 can be logically segmented into equally-sized, substantially square shaped logical fields 111. Each logical field 11 can be assigned to, i.e., covers, a corresponding electro-magnetic actuator 120.

FIG. 3 schematically and partially shows different pre-calculated routes 40' and 41' comprising reserved fields 111. The routes 40' and 41', differing from the routes 40 and 41 depicted in FIG. 2, have an intersection.

In a time-prioritized reservation scheme, a plurality of, for example 10, logical fields 111 lying on the routes 40' and 41' can be reserved for sample container carriers to be moved on the routes 40' and 41'. In other words, the logical fields 111 can be reserved in a first come, first serve manner for each sample container 140 carrier to be moved.

Given that for a sample container carrier to be moved on route 40' the logical fields 111 on the route 40' have been reserved before the logical fields 111 on the route 41' have been reserved for another sample container carrier to be moved on route 41', the sample container carrier moving on route 41' can stop before reaching the field in the intersection of the routes 40' and 41', thus avoiding a potential collision. The reserved fields 111 can be released when the sample container carriers have passed the reserved fields 111.

After the initialization of the laboratory sample distribution system 100, operating data of the laboratory sample distribution system 100 can be collected. The operating data can comprise information regarding a volume of traffic on the routes 40, 41, 42. During a next initialization of the laboratory sample distribution system 100, the routes 40, 41, 42 can be pre-calculated additionally depending on the volume of traffic. For example, a number of lanes assigned to the routes 40, 41, 42 can be determined depending on the volume of traffic. As depicted in FIG. 3, respective single lanes of logical fields 111 can be assigned to the routes 40' and 41'. If, for example, the volume of traffic on route 40' would be above a given threshold, a second (third, etc.) lane of logical fields 111 can be assigned to the route 40'.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

For the purposes of describing and defining the present disclosure, it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. A method of operating a laboratory sample distribution system, the method comprising:

providing the laboratory sample distribution system comprises a plurality of container carriers, wherein each container carrier comprises at least one magnetically active device and carries a sample container containing a sample; and a transport device comprising a transport plane to carry the plurality of container carriers, a plurality of electro-magnetic actuators stationary arranged below the transport plane, wherein the electro-magnetic actuators move a container carrier placed on top of the transport plane by applying a magnetic force to the container carrier, wherein the transport plane is configured to support the sample container carriers, wherein the transport plane comprises a plurality of transfer locations, wherein the transfer locations are assigned to corresponding laboratory stations, and a drive, wherein the drive is configured to move the sample container carriers on the transport plane;

initializing the system, wherein initializing the system includes pre-calculating fixed routes on the transport plane between the transfer locations;

after initialization of the laboratory sample distribution system, collecting operating data of the laboratory sample distribution system including determining the number of container carriers being moved; and subsequently controlling the drive such that all sample container carriers move along the same pre-calculated fixed routes on the transport plane; and during a next initialization of the laboratory sample distribution system, pre-calculating the routes additionally depending on the operating data, wherein the operating data comprise information regarding a volume of traffic on the routes.

2. The method according to claim 1, wherein the routes are calculated using an informed search algorithm.

3. The method according to claim 1, wherein the informed search algorithm is an A*-algorithm or a D*-algorithm.

4. The method according to claim 1, wherein the routes are calculated such that a number of intersections between different routes are minimized.

5. The method according to claim 1, wherein during the initialization of the laboratory sample distribution system, buffer areas located on the transport plane are allocated to the laboratory stations, wherein samples waiting to be analyzed by the laboratory stations are buffered in the buffer areas.

6. The method according to claim 5, wherein the buffer areas are allocated such that the pre-calculated routes do not intersect the buffer areas.

7. The method according to claim 5, wherein sample container carriers are entered into the buffer areas or removed from the buffer areas over the transfer locations.

8. The method according to claim 1, wherein the transport plane is segmented into logical fields, wherein in a time-prioritized reservation scheme, an adjustable number of logical fields positioned on a pre-calculated route is reserved for sample container carriers movement, wherein the sample container carriers movement on the pre-calculated routes comprise reserving logical fields with a higher time priority than for other sample container carriers.

9. The method according to claim 1, wherein pre-calculating the routes comprises that a plurality of lanes assigned to the routes is determined depending on the volume of traffic.

10. The method according to claim 1 wherein samples and/or sample containers and/or sample container carriers are transferred to/from the laboratory stations using the transfer locations.

11. The method according to claim 1, wherein during initialization of the laboratory sample distribution system, the routes are pre-calculated between the transfer locations.

12. A laboratory sample distribution system, the laboratory sample distribution system comprising:
- a plurality of container carriers, wherein each container carrier comprises at least one magnetically active device and carries a sample container containing a sample;
- a transport device comprising a transport plane to carry the plurality of container carriers, a plurality of electro-magnetic actuators stationary arranged below the transport plane, wherein the electro-magnetic actuators move a container carrier placed on top of the transport plane by applying a magnetic force to the container carrier, wherein the transport plane is configured to support the sample container carriers, wherein the transport plane comprises a plurality of transfer locations, wherein the transfer locations are assigned to corresponding laboratory stations;
- a drive, wherein the drive is configured to move the sample container carriers on the transport plane; and
- a control unit, wherein the control unit is configured to:
    - initialize the system, wherein initializing the system includes pre-calculating fixed routes on the transport plane between the transfer locations;
    - after initializing the laboratory sample distribution system, collecting operating data of the laboratory sample distribution system including determining the number of container carriers being moved; and
    - subsequently controlling the drive such that all sample container carriers move along the same pre-calculated fixed routes on the transport plane; and
    - during a next initialization of the laboratory sample distribution system, pre-calculating the routes additionally depending on the operating data, wherein the operating data comprise information regarding a volume of traffic on the routes.

13. A laboratory automation system, the laboratory automation system comprising a plurality of laboratory stations; and
- a laboratory sample distribution system according to claim 12.

14. The laboratory automation system according to claim 13, wherein the plurality of laboratory stations comprise pre-analytical, analytical and/or post-analytical stations.

* * * * *